(12) United States Patent
Bauer et al.

(10) Patent No.: US 11,523,747 B2
(45) Date of Patent: Dec. 13, 2022

(54) MEDICAL DIAGNOSTIC SYSTEM WITH EVENT DRIVERS

(71) Applicant: Siemens Healthcare GmbH, Erlangen (DE)

(72) Inventors: Simon Bauer, Baunach (DE); Thorsten Feiweier, Poxdorf (DE); Christian Köglmeier, Nuremberg (DE); Carsten Prinz, Baiersdorf (DE); Daniel Nicolas Splitthoff, Uttenreuth (DE); Michael Zenge, Nuremberg (DE); Michael Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 378 days.

(21) Appl. No.: 16/733,235

(22) Filed: Jan. 2, 2020

(65) Prior Publication Data
US 2020/0214590 A1 Jul. 9, 2020

(30) Foreign Application Priority Data
Jan. 3, 2019 (DE) .......................... 102019200016.9

(51) Int. Cl.
*G01R 33/30* (2006.01)
*A61B 5/055* (2006.01)
(52) U.S. Cl.
CPC ............ *A61B 5/055* (2013.01); *G01R 33/307* (2013.01)
(58) Field of Classification Search
CPC ..... A61B 5/055; G01R 33/307; G01R 33/543
See application file for complete search history.

(56) References Cited

U.S. PATENT DOCUMENTS

2009/0043203 A1* 2/2009 Pelissier .................. A61B 8/00
600/446
2013/0127467 A1* 5/2013 Yokoi .................... G01R 33/34
324/318

FOREIGN PATENT DOCUMENTS

DE 19624516 A1 10/1997

OTHER PUBLICATIONS

German Office Action for German Application No. 10 2019 200 016.9 dated Nov. 28, 2019.
Feiweier, Thorsten et al. "Independent Application Publication for MRI Systems" Prior Art Journal 2020 #pp. 1-2. ISBN: 978-3-947591-29-9.

* cited by examiner

*Primary Examiner* — G. M. A Hyder
(74) *Attorney, Agent, or Firm* — Lempia Summerfield Katz LLC

(57) ABSTRACT

A method for operating a medical diagnostic system that is configured to use a system component of the diagnostic system to generate examination data of a person under examination during an examination procedure is provided. The examination procedure with control of the system component is controlled by a piece of control software, and a component driver exchanges control commands of the control software with the system component in order to control the system component. The method includes providing an event driver that communicates with the control software via an interface of the control software. Via the event driver, a first event is detected in the examination procedure and reported to the event driver. When the first event is detected in the examination procedure, the use of the system component in the examination procedure is modified to a first type defined by the event driver.

16 Claims, 3 Drawing Sheets

MEDICAL DIAGNOSTIC SYSTEM WITH EVENT DRIVERS

This application claims the benefit of German Patent Application No. 10 2019 200 016.9, filed on Jan. 3, 2019, which is hereby incorporated by reference in its entirety.

BACKGROUND

The present embodiments relate to operating a medical diagnostic system.

Medical diagnostic systems (e.g., imaging apparatuses such as magnetic resonance (MR) or computed tomography (CT) facilities) consist of a large amount of technical hardware or system components, with complex control software with complex software modules being necessary for the coordinated actuation thereof. For communication between the system components, the hardware, component drivers that carry out the communication between the control software and the system components in a driver layer are typically used. As a result, settings and commands may be sent to the system components, and properties, statuses, and data may be received by the system component.

Through the use of standardized communication protocols, it is possible to replace a system component A with a new or modified system component B. In this context, the associated component driver is also generally exchanged, so that the unaltered control software of the diagnostic system may communicate with and actuate the new system component via a standardized programming Interface, application programming interface (API). This makes it possible, for example, in the case of MR facilities, to use new or changed magnetic field gradient generating units or an additional signal receiving unit, such as a local receive coil, for example, without changes to the central control software of the MR facility being necessary.

It is increasingly becoming necessary, however, to apply more complex functions that were previously not provided in the protocol of the driver of the system component at a later point. This may, for example, involve functions with dependencies upon the current status of the examination procedure or depending upon the status of one or more system components. For example, it would be desirable to switch a gradient amplifier in an MR facility into a power saving mode when no measurement is immediately pending and to terminate this power saving mode immediately before starting a measurement. It would likewise be desirable, for example, to only activate a local coil for receiving the MR signals when an MR measurement is actually taking place.

The necessary commands for switching the desired setting, such as a deactivation of a power supply, for example, are usually provided in the communication protocol of the driver layer in the prior art. In order to be able to make these settings as a function of the status of the examination procedure (e.g., as a function of the status of a measurement or of a system component), however, it is necessary to expand and adapt the control software accordingly. It is thus not easily possible to make this function available in the installed diagnostic system at a later point. The desired functionality would only be able to be realized with a comprehensive and time-consuming recompilation and installation of the control software. This renewal of the control software, however, requires a great expenditure for development, testing, and release due to the high level of complexity of the control software.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the above problems may be resolved, and additional functions in a method examination procedure may be provided in a simple manner without completely renewing the control software.

In accordance with a first aspect, a method for operating a medical diagnostic system is provided. The medical diagnostic system is configured to generate examination data of a person under examination during an examination procedure while using a system component of the medical diagnostic system. In this context, the examination procedure is controlled by a piece of control software with control of the system component, where a component driver exchanges control commands of the control software with the system component in order to control the system component. Additionally, an event driver that communicates with the control software via an interface of the control software is provided. Via the event driver, a first event is detected in the examination procedure and reported to the event driver. When the first event is detected in the examination procedure, the use of the system component in the examination procedure is modified to a first type defined by the event driver.

Through the use of additional event drivers, which communicate with the control software via interfaces or expansion points of the control software, certain events in the measurement procedure may be registered, and as soon as this event occurs, defined changes that are induced by the event driver may be provided.

In this context, the control software may only be able to detect the first event, report an occurrence of the first event to the event driver, and modify the use of the system component to the first type, because of the event driver. Without changing the control software, this would not otherwise be possible.

The event driver may, for example, have data or instructions with which the first event may be identified in the examination procedure and with which it may be determined how the examination procedure is modified on detection of the first event.

In this context, the detection of the first event may signify a detection of a defined status in the procedure of the examination procedure. It is likewise possible for the detection of the first event to signify a detection of a particular status for the system component.

The medical diagnostic system may be an imaging system such as a magnetic resonance (MR) facility or a computed tomography (CT) facility. The medical diagnostic system does not necessarily need to be an imaging system, however, but may also be a system for recording spectroscopic data of the person under examination.

A second event in the examination procedure may also be detected by the event driver; when the second event is detected, the use of the system component in the examination procedure is modified to a second type defined by the event driver.

The modification of the use of the system component to the first type may signify that an operating status of the system component is changed from a first operating mode to a second other operating mode. In this context, this may provide that the system component is shifted into an idle status, in which the power supply of the system component is at least reduced. This may also signify, however, that the system component is shifted from the idle status into an active operating status, in which the system component is then used to generate the examination data of the person under examination.

In this context, the modification of the use of the system component to the second type may include setting the system component from the idle status to the active status. When detecting the first event, the system component may be set to the idle status, while the system component is set to the active operating status again when the second event is detected. For example, it may only be possible to record the examination data when the system component has been shifted from the idle status to the active operating status.

The detection of the first event or the detection of the second event may include the following events: detecting that a couch for supporting the person under examination is positioned relative to the diagnostic system such that it is possible to position the person under examination on the couch, but it is not yet possible to record the examination data; detecting that a couch for supporting the person under examination is positioned relative to the diagnostic system such that it is now possible to record the examination data; or detecting that a recording of the examination data is started or terminated.

If the diagnostic system is an MR facility, then the system component may, for example, be the couch for positioning the person under examination, the receive coil for receiving the MR signals, or a gradient system for generating the magnetic field gradients. Other system components such as the RF unit for generating the RF pulses may also play the role of the system component.

In addition, the medical diagnostic system is provided. The medical diagnostic system has the system component that is used to generate examination data of the person under examination during an examination procedure. A memory unit and at least one processor unit are provided. The memory unit stores the control software, via which the examination procedure is controlled when the control software is executed in the at least one processor unit, while using the system component. The memory unit further stores at least one component driver that exchanges control commands of the control software with the system component in order to control the system component. The memory unit likewise stores event drivers. An event driver communicates with the control software via an interface. If the event driver is used, the diagnostic system is embodied to perform methods as have been explained above, or as described in the following.

In addition, a computer program product is provided. The computer program product includes one or more programs (e.g., instructions) that be loaded directly into a memory unit of the processor unit of the medical diagnostic system in order to carry out the acts for operating the diagnostic system, as have been explained above.

In addition, an electronically readable data carrier (e.g., a non-transitory computer-readable storage medium) is provided with electronically readable control information (e.g., instructions) stored thereon. The control information is configured such that a method as outlined above is performed when the data carrier is used in a processor unit of the diagnostic system.

DETAILED DESCRIPTION

Figure 1:
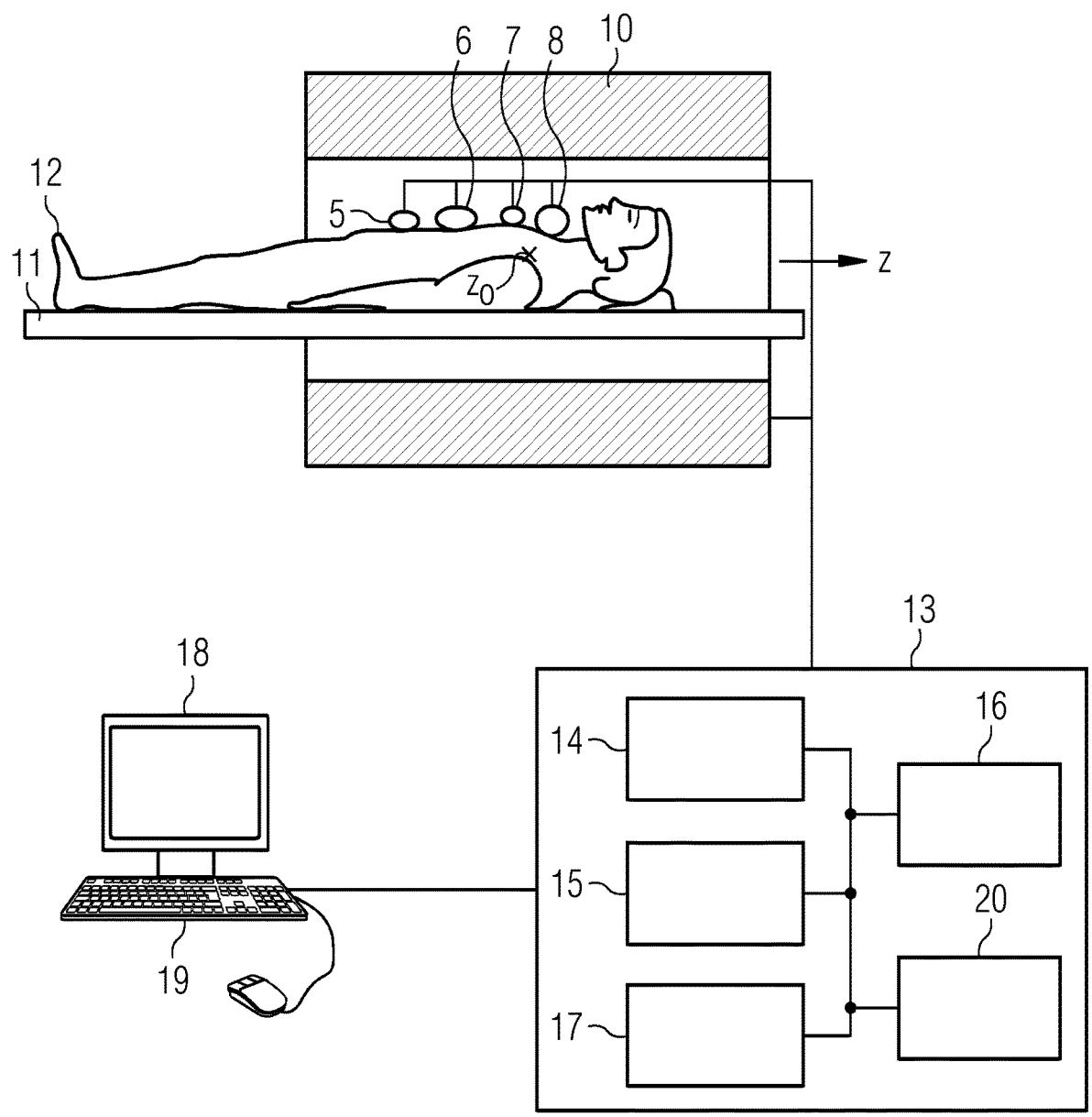
FIG. 1 schematically shows one embodiment of a medical diagnostic system.

The present embodiments are described in greater detail below with reference to the drawings. In the drawings, the same reference characters indicate the same or similar elements. The figures are schematic representations of various embodiments. The elements shown in the figures are not necessarily shown to scale. Rather, the elements are reproduced such that the function and purpose are comprehensible to the person skilled in the art. The connections shown in the figures between functional units or other elements may also be implemented as an indirect connection, where a connection may be wireless or wired. Functional units may be implemented as hardware, software, firmware, or a combination thereof.

With reference to FIG. 1, the present embodiments are described in connection with a magnetic resonance (MR) facility as an imaging apparatus. The MR facility, however, may also be used purely as a spectroscopic facility that compiles spectroscopy data of a person under examination. However, other medical diagnostic systems such as, for example, computed tomography (CT) systems or positron emission tomography (PET) facilities may also be provided.

The MR facility shown in FIG. 1 has a magnet 10 for generating a polarization field BO, where a person under examination 12 arranged on a couch 11 is moved into the magnet 10 in order to record spatially encoded magnetic resonance signals of the person under examination 12 there. For the signal recording, the coil elements 5 to 8 are shown by way of example. By applying radio-frequency pulses and by switching magnetic field gradients, the magnetization generated by the polarization field BO may be deflected out of the equilibrium position and spatially encoded, and the resulting magnetization is detected by the receive coils. The principles of how MR images may be generated by irradiating RF pulses and by switching magnetic field gradients in various combinations and sequences are known to a person skilled in the art and will not be explained in further detail here.

A control unit 13 that may be used to control the MR facility is provided. The control unit 13 has a gradient control unit 14 for controlling and switching the necessary magnetic field gradients. The control unit 13 also has a radio frequency (RF) control unit 15 provided for controlling and generating the RF pulses for deflecting the magnetization. An image sequence controller 16 controls an order of the magnetic field gradients, signal detection, and the RF pulses, and thus, indirectly controls the gradient control unit 14, the receive coils, and the RF control unit 15. Via an input unit 19, an operator may control the MR facility, and MR images and other information necessary for the control may be displayed on a display 18. A processor unit 17 (e.g., a processor) is provided for controlling the various units in the control unit 13. A memory 20, in which, for example, program modules or control software that are necessary for operating the MR facility and the individual components, such as receive coils, RF units, etc., is provided. For communication with the individual system components, the memory 20 also has component drivers. The control software has expansion points or interfaces, with which event drivers may be used in addition to the components or hardware drivers. These event drivers log on at the control software via the expansion points or interfaces and are thus able to register events of the measurement procedure. As soon as one of these events occurs, the event driver obtains a corresponding notification. Conversely, the expansion points or interfaces of the control software may also be embodied such that an event driver may trigger particular events in the control software. In this manner, the event driver may influence the examination procedure. To expand an existing MR facility with complex functions at a later point, all that is needed is the delivery of the event driver, in addition to the necessary hardware, such as a system component, and the component driver. This involves a software component with low complexity, whereby the development, testing, and release expenditure may be kept low.

Figure 2:
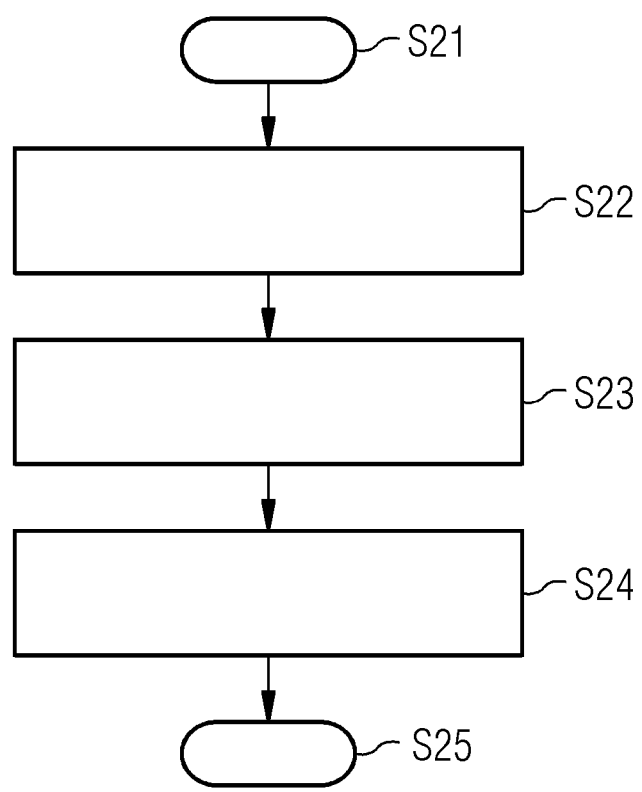
FIG. 2 schematically shows a flow diagram with acts illustrating how additional functions may be implemented without changing control software.

In FIG. 2, several fundamental acts are shown, illustrating how the event drivers may be used to install additional functions for certain components of the MR facility, without completely renewing the control software. The method begins at act S21. At act S22, the event driver is stored in the memory unit of the MR facility or of the medical diagnostic system, where the event driver communicates with the control software of the MR facility via an interface. The event driver has data that enables identification of a first event in the examination procedure, where the event driver also stipulates how the examination procedure is changed when the event is detected. Detecting the event may involve detecting a particular act in the method procedure (e.g., starting a measurement), or detecting the event involves detecting a defined status of a system component (e.g., when the patient couch 11 lies in a particular defined position). Via the event driver, the control software is now able to detect the event defined by the event driver (act S23). This information is transferred to the event driver, and the examination procedure is modified by the event driver in act S24. The modification of the examination procedure may involve changing the status at the system component. For example, a system component such as the couch is moved in a particular direction, or an operating status of a system component changes (e.g., a system component is set to a power saving mode or an active operating mode). The method ends in act S25.

Figure 3:
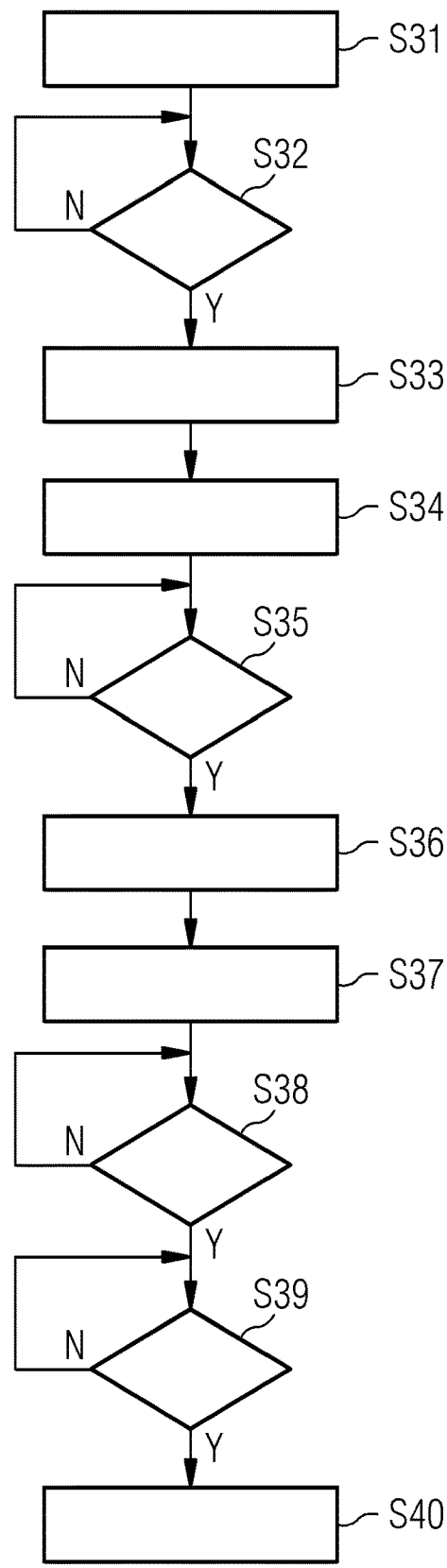
FIG. 3 shows a flow diagram of a further embodiment showing how additional functions may be implemented without changing the control software.

A first example for the use of the event driver is described in connection with FIG. 3. In act S31, an event driver is stored in the memory unit of the MR facility and enters into communication with the control software. For example, the event driver may register the event that the couch 11 is completely moved out from the MR facility, the event that the couch 11 is moved back into the MR facility, and the event that the actual MR measurement is starting. Further, the event driver may declare the event of a standby status to the system controller. As soon as the event occurs in the procedure that the couch 11 is completely moved out from the facility, the control software reports this event to the driver (act S32). Subsequently, the function driver reports the standby status to the control software in act S33. The standby status stipulates that an actual MR measurement will not take place in the near future, and it is possible in act S34 to shift the gradient amplifier into the power saving mode via the component driver (act S34). In act S35, the event driver now monitors whether the couch 11 is moved back into the MR facility. If this is the case and the event driver obtains this information from the control software, then in act S36, the gradient amplifier is taken out of the power saving mode; in step S37, the standby status of the gradient amplifier is canceled. If the event driver obtains the information that the measurement is to be started in act S38, then in act S39, it is checked whether all standby statuses have been canceled. Then, the measurement may be started in act S40.

Figure 4:
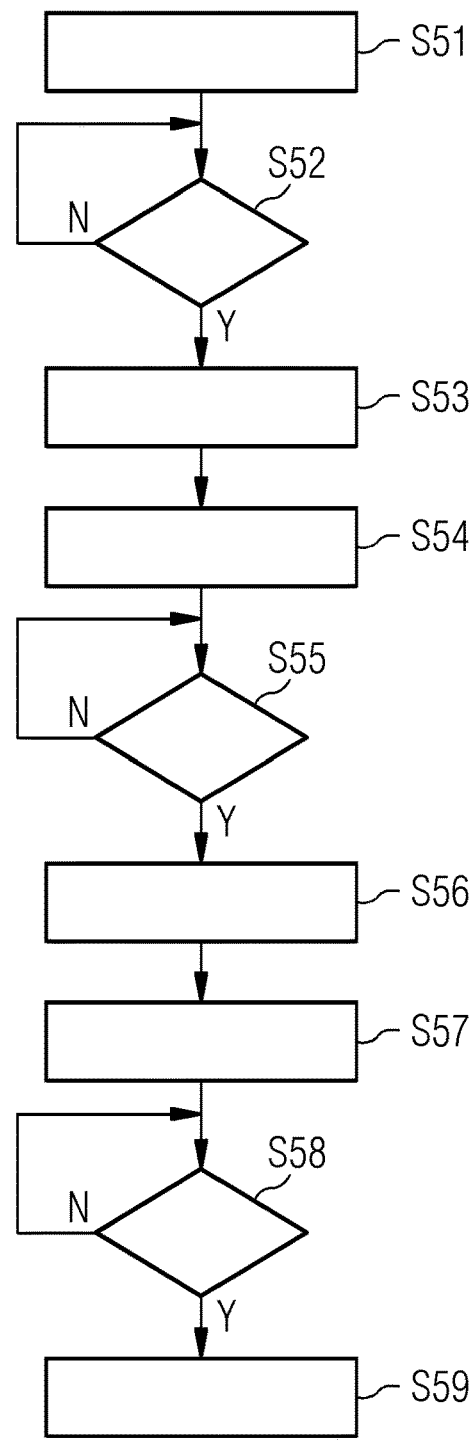
FIG. 4 shows a further example of a flow diagram with acts for carrying out additional functions without changing the control software.

A further exemplary embodiment is described in connection with FIG. 4. In this context, the event driver registers the event that a measurement is started, and that a measurement is terminated. In addition, the event of the standby status is declared. This event driver may be loaded into the memory in act S51 in order to communicate with the control software. The control software subsequently checks in act S52 whether a measurement has been terminated. If this is the case, then this is reported to the event driver, so that the event driver detects in act S52 that the actual MR measurement has been terminated. In act S53, the event driver is thus able to report to the control software that a standby status is present. This may involve a standby status of the control software that is not related to the component. The control software recognizes the standby status, and the standby status may be triggered by an event. It is not possible to start a measurement in the standby status. This may also involve a component-related standby status (e.g., of the coil or the coil controller). The coil controller "recognizes" a standby status, and this standby status may be triggered by an event. The control software may query the measurement-readiness of the coil control: if the coils are not ready for measurement (which is the case in the standby status of the coil control), then no measurement may be started. The standby status is "indirectly" communicated to the control software in this manner. In act S54, the voltage supply of the system component, such as the receive coils, for example, is switched off via the component driver. In act S55, it is now checked whether the control software provides the information that a measurement is to be started. If this is the case in act S55, then in act S56, the voltage supply is switched on again; in act S57, the standby status is canceled again after a defined pause. In act S58, it is checked whether all the standby statuses have been canceled; if this is the case, the actual MR measurement may begin in act S59.

The exemplary embodiments described above show that, by way of the described concept of the event driver, the possibility of installing interactions between a system component and a measurement procedure that are complex and not provided at the point in time of delivering the control software may be provided with a low expenditure at a later point. These may thus be made available for the operator.

The described embodiments make it possible to use complex new hardware functions at a later point, without changes, tests, or releases of the control software being necessary.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical diagnostic system that is configured to use a system component of the medical diagnostic system to generate examination data of a person under examination during an examination procedure, wherein the examination procedure with control of the system component is controlled by a piece of control software, and a component driver exchanges control commands of the control software with the system component, such that the system component is controlled, the method comprising:
   providing an event driver that communicates with the control software via an interface of the control software, the event driver and the interface being software;
   detecting, via the event driver, a first event in the examination procedure and reporting the detected first event to the event driver; and
   modifying the use of the system component in the examination procedure to a first type defined by the event driver when the first event is detected in the examination procedure.

2. The method of claim 1, wherein it is only due to the event driver that the control software is operable to detect the first event, report an occurrence of the first event to the event driver via the interface, and modify the use of the system component in the examination procedure to the first type.

3. The method of claim 1, further comprising:
   detecting, by the event driver, a second event in the examination procedure; and
   modifying the use of the system component in the examination procedure to a second type defined by the event driver when the second event is detected.

4. The method of claim 3, wherein changing the operating mode to the second operating mode comprises:
   setting the system component to an idle status, in which a power supply of the system component is at least reduced; or
   setting the system component from the idle status, in which the power supply of the system component is at least reduced, to an active operating status, in which the system component is usable to generate the examination data.

5. The method of claim 1, wherein modifying the use of the system component in the examination procedure to the first type comprises changing an operating status of the system component from a first operating mode to a second operating mode, the second operating mode being different than the first operating mode.

6. The method of claim 5, wherein modifying the use of the system component to the second type comprises setting the system component from the idle status, in which a power supply of the system component is at least reduced, to an active operating status, in which the system component is usable to generate the examination data.

7. The method of claim 6, wherein recording the examination data is only possible when the system component has been set to the active operating status.

8. The method of claim 1, wherein detecting the first event comprises:
   detecting that a couch for supporting the person under examination is positioned relative to the medical diagnostic system such that the person under examination is positionable on the couch, but the examination data is not recordable;
   detecting that a recording of the examination data is started or terminated; or
   detecting that the couch for supporting the person under examination is positioned relative to the diagnostic system such that the examination data is recordable.

9. The method of claim 1, wherein the event driver has data with which the first event is identifiable in the examination procedure and with which it is determinable how the examination procedure is modified on detection of the first event.

10. The method of claim 1, wherein detecting the first event comprises:
    detecting a defined status in the procedure of the examination procedure; or
    detecting a particular status at the system component.

11. The method of claim 1, wherein the medical diagnostic system is an imaging system.

12. The method of claim 11, wherein the imaging system is a magnetic resonance (MR) facility, and the system component is a couch for positioning the person under examination, a gradient system for generating magnetic field gradients, or a receive coil for receiving MR signals.

13. A medical diagnostic system comprising:
    a system component configured to generate examination data of a person under examination during an examination procedure;
    a memory;
    at least one processor,
    wherein the memory is configured to store a piece of control software, via which the examination procedure is controlled when the control software is executed by the at least one processor, while using the system component,
    wherein a component driver is configured to exchange control commands of the control software with the system component, such that the system component is controlled,
    wherein the memory is further configured to store an event driver that communicates with the control software via an interface of the control software, the event driver and the interface being software, and
    wherein the medical diagnostic system is configured, when using the event driver, to:
      detect, via the event driver, a first event in the examination procedure; and
      change use of the system component in the examination procedure to a first type defined by the event driver when the first event is detected in the examination procedure.

14. The medical diagnostic system of claim 13, wherein the medical diagnostic system is an imaging system.

15. The medical diagnostic system of claim 14, wherein the imaging system is a magnetic resonance (MR) facility, and the system component is a couch for positioning the person under examination, a gradient system for generating magnetic field gradients, or a receive coil for receiving MR signals.

16. In a non-transitory computer-readable storage medium that stores instructions executable by one or more processors of a medical diagnostic system to operate the medical diagnostic system, such that a system component of the diagnostic system is used to generate examination data of a person under examination during an examination procedure, wherein the examination procedure with control of the system component is controlled by a piece of control software, and a component driver exchanges control commands of the control software with the system component, such that the system component is controlled, the instructions comprising:
   providing an event driver that communicates with the control software via an interface of the control software, the event driver and the interface being software;
   detecting, via the event driver, a first event in the examination procedure and reporting the detected first event to the event driver; and
   modifying the use of the system component in the examination procedure to a first type defined by the event driver when the first event is detected in the examination procedure.

* * * * *